Figure 1:
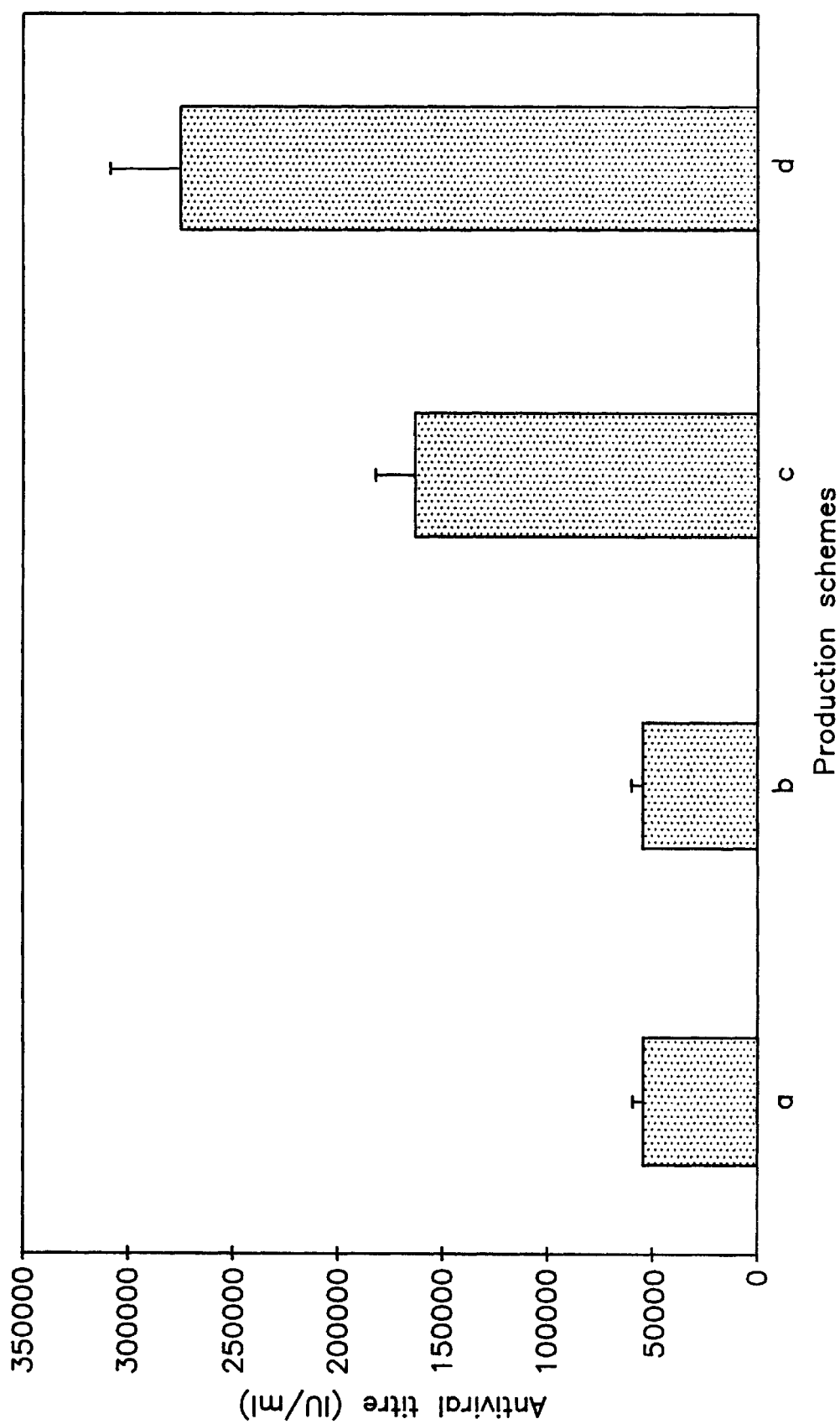

United States Patent

Bassily et al.

[11] Patent Number: 6,156,542
[45] Date of Patent: Dec. 5, 2000

[54] METHOD FOR PRODUCTION OF NATIVE HUMAN LEUKOCYTE (ALPHA) INTERFERON

[75] Inventors: George Sabet Bassily; Haider A. Galeb; Mervat Attalla Mikhael, all of Cairo, Egypt

[73] Assignee: ACAPI, Alpha-Chem Advanced Pharmaceutical Industries, S.A.E., Cairo, Egypt

[21] Appl. No.: 09/076,194

[22] Filed: May 12, 1998

[30]     Foreign Application Priority Data

Mar. 3, 1998 [HU] Hungary ................................. 9800554

[51] Int. Cl.⁷ ...................................................... C12P 21/04
[52] U.S. Cl. .......................................... 435/70.5; 435/70.4
[58] Field of Search .................................... 435/70.5, 70.4

[56]         References Cited

U.S. PATENT DOCUMENTS 5,240,864  8/1993  Koga ....................................... 436/547

OTHER PUBLICATIONS

Fraenkel–Conrat et al., "Virology", 1982, Prentice–Hall, pp. 306–309.
ATCC Cell Lines and Hybrodomas, 1994, p. 518.
Fierlbeck and Rassner, J. Interferon Res., 9(Suppl. 2), p. S221, 1989.
Boccara et al., J. Interferon Res., 11(Suppl. 1), p. S242, 1991.
Kikuta et al., J. Gen. Virol., 65, p. 837–841, 1984.
Roberts et al., J. Immunol. 123, p. 365–369, 1979.
Saksela et al., Prog. Med. Virol., 30, p. 78–86, 1984.

*Primary Examiner*—Irene Marx
*Attorney, Agent, or Firm*—Birch, Stewart, Kolasch & Birch, LLP

[57]         ABSTRACT

The invention relates to a process for the preparation of natural human alfa interferon from human blood by ammonium chloride haemolysis and purification by washing with buffered physiological saline solution, then preparing a suspension in a liquid culture medium and induction by Sendai virus. The process according to the invention is characterized in that leukocytes are separated from human blood, purified in a known way, suspended in a liquid culture medium, then induced by Sendai virus, and the pretreatment is carried out at 30–40° C., 60–90 minutes after the induction the incubation is continued at 30° C. or at a lower temperature, at the end of incubation further quantity of Sendai virus is added to the suspension, then the cells are separated, and the pH of the supernatant is made acidic.

13 Claims, 3 Drawing Sheets

METHOD FOR PRODUCTION OF NATIVE HUMAN LEUKOCYTE (ALPHA) INTERFERON

The invention relates to a process for the preparation of natural human leukocyte (alfa) interferon.

The natural human alfa-interferon consists of proteins of low molecular weight (18–26 kD) which are present in a physiological ration (Goren et al., J. Interferon Res., 6. pp 323–329, 1986). This mixture possesses several different biological activity. Among others its antiviral (von Wussow & Jakschies, in Interferon, ed. Niederle & von Wussow, Springer-Verlag, Berlin, pp 79–91, 1990), antibacterial (Bukholm et al., Antivir. Res., 1984, Abstr. 1(3), p 70; Niesel et al, J. Interferon Res., 9(Suppl.2.), p S223, 1989), cell proliferation inhibiting (Samid, Interferons and Cytokines, 11, pp 38–40, 1989; Clemens & McNurlan, J. Biochem., 226, pp 545–360, 1985), immune function stimulating (Maudsley et al., Immune Responses, Virus Infections and Disease, pp 15–33, ed. Dimmock & Minor, IRL Press, Oxford, 1989; Vilcek & DeMayer eds., Interferon 2; Interferons and the Immune System, Elsevier Science Publishers, 1984; Virelizer, in Immune Responses, Virus Infections and Disease, pp 1–14, ed. Dimmock & Minor, IRL Press, Oxford, 1989) and antiinflammatory properties (Lemmel & Obert, J. Interferon Res., 11(suppl.1), p S76, 1991; Lemmel et al., Rheumatology, 7, pp 127–132, 1987; Mécs et al., in Abstracts of the ARES Serono Symposium on the Interferon System, p 122, 1985) are known.

On the bases of the properties mentioned above the human interferon is applied as therapeutic agent for the treatment of viral infections (Eddleston & Dixon, eds., Interferons in the Treatment of Chronic Virus Infection of the Liver, Pennine Press, Macclesfield, 1990; Levin et al., Israel J. Med. Sci., 25, pp 364–372; Arvin et al., J. Infect. Dis., 133(Suppl), pp A205–A210, 1976), tumorous diseases (Spiegel, Cancer, 59, pp 626–631, 1987; Roberts, Br. Med. J. 305, pp 1243–1244, 1992; Goldstein & Laszlo, Cancer Res., 46, pp 4315–4329, 1986) and inflammations of autoimmun origin Fierlbeck & Rassner, J. Interferon Res., 9(Suppl.2.), p S221, 1989; Boccara et al., J. Interferon Res., 11(Suppl.1.), p S242, 1991; Facon et al, Br. J. Haematol., 82, p 464, 1991) as well as in case of bacterial infections which can not be treated in other way or are very difficult to treat (Badaro et al., J. Interferon Res., 9(Suppl.2.), p S134, 1989; Kaplan et al., J. Interferon Res. 9(Suppl.2.), p S133, 1989; Gauci, Interferons Today and Tomorrow, 8, pp 37–38, 1988).

It is known that in human leukocytes interferon (IFN-alfa) production can be induced by viruses or double-stranded RNA. (Kikuta et al., J. Gen. Virol., 65, pp 837–841, 1984; Roberts et al., J. Immunol., 123, pp 365–369, 1979; Saksela et al., Prog. Med. Virol., 30, pp 78–86, 1984).

The production of natural interferon is limited by the fact, that the preparation of INF in a substantial quantity requires the collection of leukocytes from a high number of donors. According to the conventional processes (Cantell et al., In Vitro Monograph, 3, pp 35–38, 1974; Mécs et al., Hungarian Patent Application No. 2435/80; Tóth, M. et al., Eur. pat. 8411.5123.6; Tóth M et al., Acta Microbiol. Hung., 31, pp 61–67, 1984) leukocytes are recovered by centrifuging the blood taken from donors and separating the so called "buffy coat", which is rich in leukocytes.

The quantity of the blood that can be taken from one donor is sufficient for the preparation of 80–150 ml of crude interferon. Though the therapeutic value of the natural IFN-alfa exceeds that of the IFN-alfa prepared by gentechnological way (Öberg & Alm, J. Interferon Res., 9(Suppl.1.), pp S45–S51, 1989; von Wussow et al., Lancet, i, pp 882–883, 1988; von Wussow & Jakchies, ibid.), the limited number of donors and the increasing number of haematogenic virus infections (Hepatitis B, C, E viruses, HIV etc.) set measure on the quantity of natural IFN-alfa that can be produced. Thus, the quantity of natural IFN-alfa that can be prepared at present is far not enough to cover the needs.

There are two possibilities for the solution of this problem, we can try to increase either the quantity of leukocytes obtainable from one donor or the quantity of the specific IFN-alfa produced by one cell.

The aim of our invention is to enhance the IFN-alfa productivity/one donor both by increasing the quantity of leukocytes and by increasing the specific IFN production.

Our invention is based on several discoveries.

Firstly, the quantity of leukocytes obtained from one donor can be substantially increased if not the whole blood is taken from the donor but the leukocytes are separated by centrifuging the blood in a flush-type rotor and the other components of the blood are recycled into the donor's organism.

Secondly, in the coarse of IFN productions the quantity of IFN can be enhanced if after the first 90 minutes of the production the incubation temperature is decreased from 37° C. to 30° C., preventing the production of the material inhibiting the IFN production.

Thirdly, during the manipulation of leukocytes a stress protein forms in these cells and this can be liberated from the cells by adding Sendai virus to the cell suspension at the end of incubation, and with this protein also the antiviral therapeutic value of our IFN preparation can be enhanced.

Thus, the subject of the present invention is a process for the preparation of natural human IFN-alfa by haemolysis with $NH_4Cl$ and purification by washing with buffered physiological saline solution, then preparing a suspension in liquid culture medium and inducing the production by Sendai virus.

The process is charaterized in that the leukocytes are recovered from human blood, purified in a known way, then suspended in a liquid culture medium and induced by Sendai virus, the pre-treatment is carried out at 30–40° C., 60–60 minutes after the induction the incubation is continued at 30° C. or at lower temperature, at the end of incubation a further portion of Sendai virus is added to the suspension, then the cells are separated, and the pH of the supernatant is made acidic. The crude natural IFN-alfa preparation obtained above is stored at 4° C. or at −20° C.

The subject of our invention is illustrated by the following example.

EXAMPLE 1

Venous catethers are introduced in both arms of a healthy donor. The blood flowing out via one of the catethers is conducted into a flush-type rotor centrifuge where the leukocytes are separated and the other components of the blood are recycled into the donor's other arm via the other catether. In this way leukocytes can be recovered from 1–3.5 liter, preferably 2.5 liter of blood from one donor, and this results in a 4–8 times higher quantity of leukocytes compared to the quantity obtainable by known leukocyte recovery technology.

The recovered leukocytes are separated from the remaining red blood cells by gradient centrifuging (e.g. applying Ficoll, Percoll or polyethylene glycol) or preferably by haemolysis with ammonium chloride (Tóth, M. et al., Hungarian Patent Specification, No. 192 254, 1983).

The decomposed red blood cells and the leukocytes are separated (e.g. by centrifuging) and the traces of serum are washed out with a physiological solution, preferably with 0.83% saline solution stabilized with 20 mM $KH_2PO_4$ solution by adding 4–15 parts, preferably 9 parts of buffered saline solution to one part of cell suspension, then suspending the mixture homogeneously and removing the wash liquor in a suitable way (e.g. by centrifuging).

Then the purified leukocytes are suspended in a nutritive solution suitable for maintaining of cells (e.g. Eagle minimal essential culture medium and its different modifications—Dulbecco, Glasgow, Earle etc. modified Eagle medium—, RPMI 1640 culture medium).

The following simple culture medium, suitable for autoclaving, can be used advantageously:

| Components | Quantity (mg/ml) |
|---|---|
| $CaCl_2$ | 100–400 |
| KCl | 250–600 |
| $MgSO_4$ or $MgCl_2$ | 100–500 |
| NaCl | 4500–8000 |
| $NaHCO_3$ | 200–4000 |
| $NaH_2PO_4$ | 10–250 |
| Glucose | 0–6000 |
| $Fe(NO_3)_3$ | 0–0.5 |

The protein content of the liquid culture medium is supplemented to 0.2–5 mg/ml, preferably to 1 mg/ml with human serum, preferably with human serum albumin, especially human serum free from gamma-globulin.

The liquid culture medium is also supplemented with an antibiotic, preferably with gentamicin or neomycin.

The number of cells is set to $10^6$–$10^7$/ml, preferably to $10^7$ living cell/ml.

Then the cells are subjected to alfa, beta or gamma IFN treatment. For this purpose inducer-free or purified IFN is applied in 10–1000 IU/ml, preferably 200 IU/ml end concentration.

The pre-treatment is carried out at 30–40° C., preferably at 37° C. for 0.5–6 hours, preferably for 2 hours.

Then living, crude or purified Sendai virus is added to the cell suspension to 10–1000, preferably to 200 haemagglutination unit/ml end concentration. The suspension is incubated for 0.5–3 hours at 35–39° C., preferably at 37° C., then the temperature is decreased to 28–30° C., preferably to 30° C., and the incubation is continued for 6–36 hours, preferably for 15–18 hours.

At the end of incubation further 10–1000, preferably 200 haemagglutination unit/ml of Sendai virus is added to the mixture, then the cells are separated from the incubation medium e.g. by centrifuging.

The supernatant is acidified to pH 2 with a suitable agent (e.g. concentrated hydrochloric acid) and kept at 4° C. for 6–48 hours, preferably for 24 hours.

Then the hydrogen ion concentration is set on pH 6.5–8.0, preferably to 7.4 with 5 M sodium hydroxide, and the crude natural IFN-alfa preparation obtained in this way is kept at 4° C. or at −20° C. till further use.

EXAMPLE 2

Native human leukocyte interferon α production runs were performed using:

a) Mixed human leukocyte suspension (white blood cells obtained from at least 35 different donors of random blood groups) at a concentration of $10^7$ cells/ml in Eagle's Minimal Essential Medium applying 2 hours priming pretreatment by 200 International Antiviral Units/ml HuIFN-α, induction by 200 Haemagglutination Units/ml Sendai virus (Cantell strain), incubated for 16 hours at 37° under continuous stirring at 60 rpm by magnetic stirrer. Batch sizes were 1–1.2 liters.

b) As in a) except that the simplified incubation medium described in this patent application was applied instead of Eagle's Minimal Essential Medium.

c) As in b) except that a temperature shift from 37° C. to 30° C. was introduced at 90 min. after induction.

d) As in c) except that before harvesting the product (after 16 hours incubation period) a second virus challenge was performed by adding another 200 Haemagglutination Units/ml of Sendai virus. Harvesting by centrifugation (3000 g, +4° C., 30 min) immediately followed the addition of the second lot of Sendai virus.

Production comparison was done by dividing the same lot of leukocyte mixture for use under different conditions described above. Each conditions were tested in at least 5 independent production runs. The data obtained are presented in FIG. 1.

EXAMPLE 3

Figure 2:
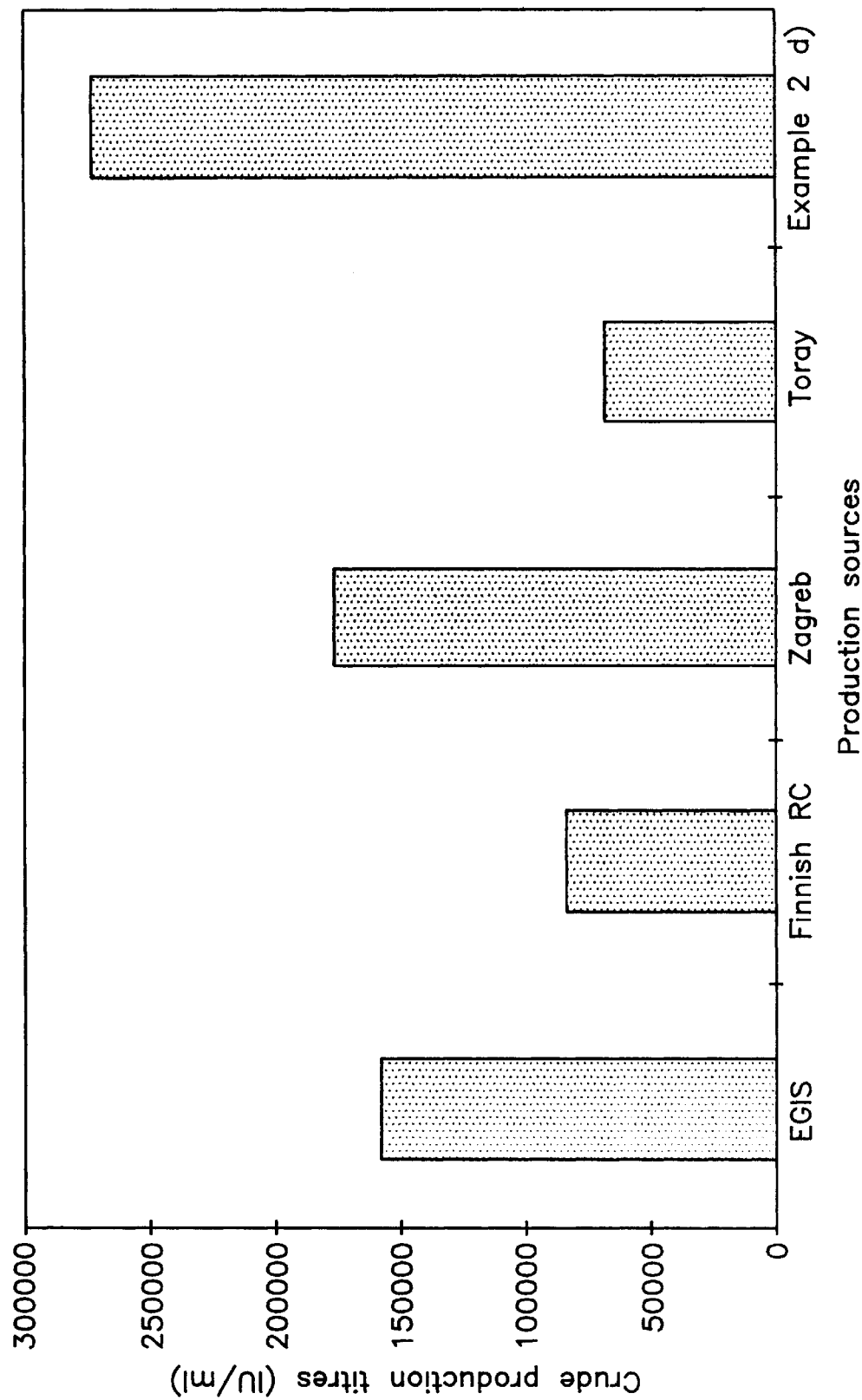
Figure 3:
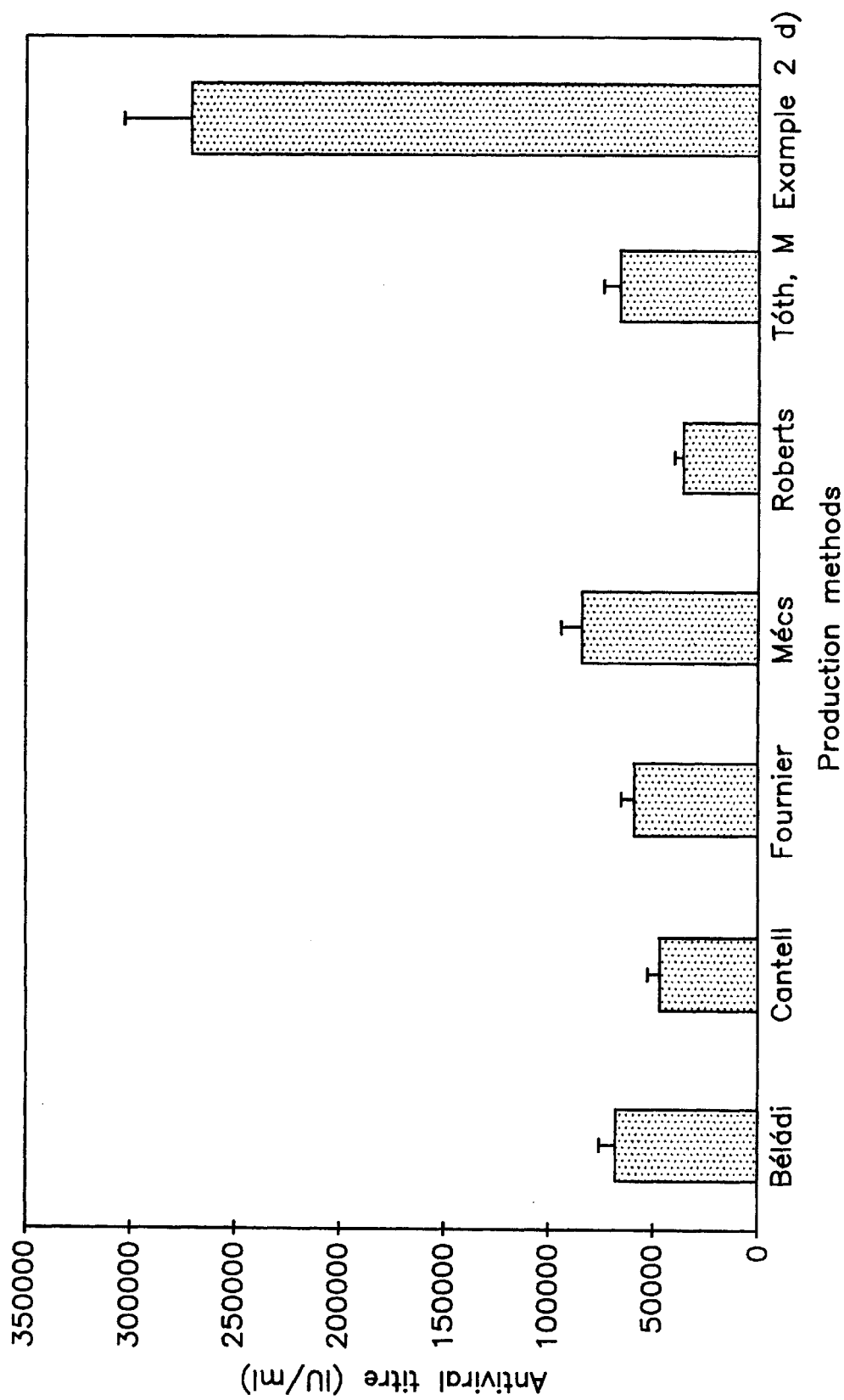

Native human leukocyte interferon α production runs were performed as described in point d) of Example 2. and compared to several other production rates described in literature. FIG. 2. shows the crude interferon liters of some commercial production sources (EGIS Pharmaceutical Co., Hungary; Finnish Red Cross; Immunological Factory of Univ. Zagreb, Croatia; Toray Co. Ltd., Japan) in comparison to the titers obtained by the protocol described above. FIG. 3. shows antiviral titers of native human interferon α produced by the patent authors by different methods described in the literature (Béládi et al.: in: The Clinical Potential of Interferons, ed R. Kono and I. Vilcek; Univ. of Tokyo Press, pp 31–38., 1982; Cantell, K. & Hirvonen, S.; Tex. Rep Biol. Med., 35, pp 138–144, 1977; Fournier et al.,; J. Immunol., 99, pp 1036–1041, 1967; Mécs et al.: Hung. Pat. No. 2435/80., 1980; Roberts et al.: J. Immunol., 123, pp 365–369., 1979; Tóth M. et al.: Acta Microbiol. Hung., 31(1), pp 61–67) in comparison to the one by the method in point d) of Example 2.

What we claim is:

1. A process for producing crude α-interferon comprising:
   i) obtaining purified leukocytes from human blood;
   ii) culturing said leudocytes in a medium in suspension culture;
   iii) adjusting the temperature of the culture to 30 to 40° C. and pretreating the culture by contacting said leukocytes with 10–1000 IU/ml α-interferon, β-interferon or γ-interferon and continuing the culturing of the leukocytes at 30 to 40° C. for 0.5 to 6 hours;
   iv) adjusting the temperature of the culture 35 to 39° C. and contacting the leukocytes with a first portion of 10–1000 haemagglutination units/ml of Sendai virus and continuing the culture for 0.5 to 3 hours;
   v) lowering the temperature of the culture to less than 30° C. and continuing the culture for 6 to 36 hours;
   vi) contacting the leukocytes with a second portion of 10–1000 haemagglutination units/ml of Sendai viurs; and
   vii) seperating the leukocytes from the culture medium to obtain a cell-free culture medium comprising crude α-interferon.

2. The method of claim 1, wherein the medium comprises:

| | |
|---|---|
| CaCl$_2$ | at 100–400 mg/L |
| KCl | at 250–600 mg/L |
| MgSO$_4$ or MgCl$_2$ | at 100–500 mg/L |
| NaCl | at 4.5–8.0 g/L |
| NaHCO$_3$ | at 0.2–4.0 g/L |
| NaH$_2$PO$_4$ | at 10–250 mg/L |
| Glucose | at 0–6.0 g/L |
| Fe(NO$_3$)$_3$ | at 0–0.5 mg/L. |

3. The method of claim 2, wherein in step v) the temperature is lowered to 28–30° C.

4. The method of claim 2, further comprising:
viii) adjusting the pH of the cell-free culture medium comprising crude α-interferon to pH 2 and incubating the cell-free culture medium at 4° C. for 6 to 48 hours; and
ix) neutralizing the pH of the cell-free culture medium to 6.5–8.0.

5. The method of claim 1, wherein the pretreatment step iii) is performed at 37° C. for 2 hours.

6. The method of claim 5, wherein in step v) the temperature is lowered to 28–30° C.

7. The method of claim 6, wherein the incubation period in step v) is 15–18 hours.

8. The method of claim 3, wherein the incubation period in step v) is 15–18 hours.

9. The method of claim 1, wherein said leukocytes are obtained by leukapheresis.

10. The method of claim 9, wherein in step v) the temperature is lowered to 28–30° C.

11. The method of claim 10, wherein the incubation period in step v) is 15–18 hours.

12. The method of claim 11, further comprising:
viii) adjusting the pH of the cell-free culture medium comprising crude α-interferon to pH 2 and incubating the cell-free culture medium at 4° C. for 6 to 48 hours; and
ix) neutralizing the pH of the cell-free culture medium to 6.5–8.0.

13. The method of claim 9, further comprising:
viii) adjusting the pH of the cell-free culture medium comprising crude α-interferon to pH 2 and incubating the cell-free culture medium at 4° C. for 6 to 48 hours; and
ix) neutralizing the pH of the cell-free culture medium to 6.5–8.0.

* * * * *